(12) United States Patent
Young et al.

(10) Patent No.: US 10,117,615 B1
(45) Date of Patent: Nov. 6, 2018

(54) ANALYZER CARTRIDGE WITH CAPILLARY WIPER

(71) Applicant: Nova Biomedical Corporation, Waltham, MA (US)

(72) Inventors: Chung Chang Young, Weston, MA (US); Jonathan Scott, Hollis, NH (US); Mauro DelleMonache, Dedham, MA (US)

(73) Assignee: Nova Biomedical Corporation, Waltham, MA (US)

( * ) Notice: Subject to any disclaimer, the term of this patent is extended or adjusted under 35 U.S.C. 154(b) by 0 days.

(21) Appl. No.: 15/665,693

(22) Filed: Aug. 1, 2017

(51) Int. Cl.
| | |
|---|---|
| *A61B 5/15* | (2006.01) |
| *B01L 3/00* | (2006.01) |
| *A61B 5/145* | (2006.01) |
| *A61B 5/157* | (2006.01) |

(52) U.S. Cl.
CPC .... *A61B 5/150022* (2013.01); *A61B 5/14546* (2013.01); *A61B 5/157* (2013.01); *A61B 5/150206* (2013.01); *B01L 3/50273* (2013.01); *B01L 2400/0406* (2013.01)

(58) Field of Classification Search
CPC ......... B01L 3/50273; B01L 2400/0406; A61B 5/150022; A61B 5/14546; A61B 5/150206; A61B 5/157
See application file for complete search history.

(56) References Cited

U.S. PATENT DOCUMENTS

| | | | | |
|---|---|---|---|---|
| 4,991,451 A | * | 2/1991 | Rodomista | G01N 35/1004 73/864.24 |
| 8,158,062 B2 | | 4/2012 | Dykes et al. | |
| 2004/0161368 A1 | * | 8/2004 | Holtlund | B01L 3/0275 422/68.1 |
| 2008/0228163 A1 | * | 9/2008 | Smith | B01L 3/50825 604/411 |
| 2009/0308184 A1 | * | 12/2009 | Blekher | A61B 5/1411 73/864.63 |
| 2011/0130740 A1 | * | 6/2011 | Levy | A61J 1/05 604/403 |
| 2012/0184025 A1 | * | 7/2012 | Kawata | G01N 21/07 435/287.2 |
| 2013/0130369 A1 | * | 5/2013 | Wilson | B01L 3/50825 435/289.1 |
| 2014/0356941 A1 | | 12/2014 | Bransky et al. | |

OTHER PUBLICATIONS

Alere Affinion Analyser Instructions for PACE.

* cited by examiner

*Primary Examiner* — Benjamin R Whatley (74) *Attorney, Agent, or Firm* — Robert R. Deleault, Esq.; Mesmer & Deleault, PLLC (57) ABSTRACT

A disposable test cartridge and method for a point-of-care analyzer includes a cartridge body having a plurality of chambers where each of the plurality of chambers has an opening at a top of the cartridge body, a cartridge cover connected to the cartridge body where the cartridge cover has a capillary-receiving aperture, a capillary wiper disposed within the capillary-receiving aperture where the capillary-receiving aperture is aligned with one of the plurality of chambers of the cartridge body, and a capillary element removably insertable into the cartridge cover where the capillary element has a capillary tube that extends into the capillary-receiving aperture and through the capillary wiper where a tip portion of the capillary tube extends into the cartridge body.

9 Claims, 9 Drawing Sheets

ANALYZER CARTRIDGE WITH CAPILLARY WIPER

BACKGROUND OF THE INVENTION

1. Field of the Invention

The present invention relates generally to in-vitro diagnostic analyzers. Particularly, the present invention relates to in-vitro diagnostic analyzers and cartridge modules for use in urgent care, point-of-care and physician offices.

2. Description of the Prior Art

In-vitro diagnostic analyzers have been available for several decades. The market for these types of analyzers were typically for use in a central laboratory. The central laboratory was capable of testing for a wide variety of biomedical species typically in a patient's blood and/or blood plasma. Some of the tests were/are for key parameters associated with the treatment of diabetic patients.

Lately, there appears to be an on-going shift for such testing from central laboratory testing to point-of-care sites within a hospital. This shift provides for quicker test data results, which can be important in diagnosis and treatment of certain conditions. Point-of-care testing plays an important role in the management of critically ill patients and is widely used in the operating room, emergency room and intensive care units. These tests are no longer performed exclusively by skilled medical technologists but also by multiskilled personnel including nurses, respiratory therapists, emergency personnel, physicians, and other medical staff. To meet this demand, manufacturers have had to downsize the analyzers and simplify the test procedures so that only minimal training in performing the test procedures is required.

One key feature common to all point-of-care analyzers is that they must be either portable and/or transportable. Examples of such point-of-care analyzers include, but are not limited to, critical care analyzers from Roche Diagnostics, a division of Hoffman-La Roche, sold under the trademarks OPTI CCA and OMNI 9, critical care analyzers from Nova Biomedical Corporation sold under the trademarks STAT PROFILE ULTRA C and CRT, CRT from Nova Biomedical Corporation, and a critical care analyzer from Dade Berhing, Inc., a division of Siemens Healthcare Diagnostics, sold under the trademark DIMENSION RXL.

More recently, there is a further shift occurring to testing in a physician's office or laboratory located within a physician's office. As testing moves away from the central laboratory, new single use medical devices have been developed to meet this need.

In the physician's office environment, there are numerous devices that utilize a capillary to collect finger stick samples for analysis. The capillary may be either glass or plastic. Typical analyses are for species such as HbA1c, lipids, etc. Once the sample is collected, these capillary-based collection devices are loaded into an analytical cartridge, which is then loaded into an instrument for analysis.

SUMMARY OF THE INVENTION

Although the point-of-care and physician office analyzers are designed to be simple to use in nature, there are issues associated with them that can lead to erroneous results. The primary factor responsible for these erroneous results is the collection of the sample.

Capillary tubes, which may be made of glass or plastic, are typically used to collect a blood sample from a finger stick. The capillary tubes used to collect the blood/sample are volumetrically very precise. If a user fails to wipe the excess blood/sample from the outside surface of the capillary tube, erroneous results may be obtained due to an over-fill situation. In other words, the sample from the outside surface is combined with the sample in the capillary tube giving a test volume that is greater than needed for the particular analysis. On the other hand, if the user does wipe off the excess sample from the outside surface of the capillary tube and fails to exercise the proper care required when doing so, the user can draw sample out of the capillary tube. This situation also leads to erroneous results due to an under-fill situation. In other words, the sample remaining within the capillary is less that the amount of sample the point-of-care analyzer is expecting to receive for the analysis. The consequence is an erroneous result.

Further, currently available point-of-care analyzers require the use of blood plasma as the sample. This requires separation of the red blood cells from the plasma in a blood sample before obtaining test results. The present invention uses whole blood samples without the need to separate the red blood cells from the plasma before testing and obtaining meaningful test results.

It is an object of the present invention to provide a point-of-care analyzer that processes whole blood samples without the need to separate the blood cells from the blood plasma.

It is another object of the present invention to provide an apparatus and method that prevents erroneous results from a point-of-care analyzer caused by an under-fill or an over-fill situation.

It is a further object of the present invention to provide an apparatus and method where a minimally-trained healthcare worker can perform sample acquisition and sample testing in a point-of-care analyzer to obtain accurate results therefrom.

It is another object of the present invention to provide an apparatus and method to obtain accurate test results from a point-of-care analyzer without the need to use a trained instrument technologist for transferring a sample to be tested into the point-of-care analyzer.

It is another object of the present invention to provide disposable test cartridge for use in a point-of-care analyzer that prevents and/or reduces the possibility of an erroneous result obtained from the point-of-care analyzer.

The present invention achieves these and other objectives by providing a device and method that ensures the correct amount of sample is presented to a disposable test cartridge for use in a point-of-care analyzer.

In one embodiment of the present invention, a disposable test cartridge for a point-of-care analyzer includes a cartridge body having a plurality of chambers where each of the plurality of chambers has an opening at a top of the cartridge body, a removable cartridge cover connected to the cartridge body and having a capillary-receiving aperture, a capillary wiper disposed within the capillary-receiving aperture where the capillary-receiving aperture is aligned with one of the plurality of chambers of the cartridge body, and a capillary element removably insertable into the cartridge cover where the capillary element has a capillary tube that extends into the capillary-receiving aperture and through the capillary wiper where a tip portion of the capillary tube extends into the cartridge body. Because the test cartridge is disposable, some of the plurality of test chambers contain a variety of items such as, for example, specific test reagents for specific test measurements, a disposable pipette, and the like. Further, in a marketable product, a sealing tape and/or foil is positioned over the top of the cartridge body in order to prevent contamination of the test chambers and reagents as well as for extending the storage life of the disposable test cartridge.

In another embodiment of the present invention, the capillary wiper has a tubular upper portion having an upper portion opening and a tapered lower portion having a lower portion opening where the tubular upper portion and the tapered lower portion define an internal through space.

In a further embodiment of the present invention, the capillary wiper has a lower portion opening with a diameter smaller than an outside diameter of the capillary tube.

In still another embodiment of the present invention, the capillary wiper has an internal space within a lower portion that is also tapered.

In yet a further embodiment of the present invention, the capillary wiper is made of an elastomeric material.

In another embodiment of the present invention, the capillary element has a capillary element body with a top body opening in fluid communication with the capillary tube.

In one embodiment of the present invention, the cartridge cover has a wiper-receiving neck portion extending from the capillary-receiving aperture a predefined distance towards but spaced from the cartridge body.

In another embodiment, the tubular upper portion of the capillary wiper has a cylindrical recess with a diameter smaller than a diameter of the wiper-receiving neck portion of the cartridge cover.

In one embodiment of the present invention, the tubular upper portion of the capillary wiper has a lower tubular end that transitions to the tapered lower portion where the lower cylindrical end has a ledge portion that contacts the top of the cartridge body while the tapered lower portion extends into the one of the plurality of chambers of the cartridge body.

In one embodiment of the present invention, the capillary wiper has a pipette shape.

In one embodiment of the present invention, there is disclosed a capillary wiper for a disposable test cartridge for a point-of-care analyzer. The capillary wiper includes a tubular upper portion having a tubular top end, a tubular bottom end and an upper portion opening, a tapered lower portion having a base portion and an apex portion where the apex portion has a lower portion opening and where the base portion is connected to the tubular bottom end of the tubular upper portion, and an open pathway between the upper portion opening and the lower portion opening defining a volume for receiving a capillary tube therethrough. The upper portion opening has a larger cross-sectional area than the capillary tube and the lower portion opening has a smaller cross-sectional area than the capillary tube.

In one embodiment, the tapered lower portion of the capillary wiper is made of an elastomeric material.

In another embodiment, the tubular upper portion and the tapered lowered portion are made of an elastomeric material.

In still another embodiment, the entire capillary wiper is made of an elastomeric material.

In one embodiment of the present invention, the tubular upper portion of the capillary wiper is adapted for attachment to a cartridge cover of the disposable test cartridge.

In one embodiment of the present invention, the capillary wiper is over-molded into a cartridge cover of the disposable test cartridge.

In another embodiment of the present invention, the open pathway within the tapered lower portion of the capillary wiper is tapered.

In one embodiment, a method to reduce erroneous results from a point-of-care analyzer caused by over-filling and under-filling of a sample disposed in a disposable test cartridge for use in the point-of-care blood analyzer is disclosed. The method includes providing a tubular, capillary wiper having a pipette-shaped longitudinal cross-section with a tapered, elastomeric bottom portion and a top opening having a cross-sectional area greater that the cross-sectional area of a capillary tube used with the disposable test cartridge and bottom opening having a cross-sectional area smaller than the cross-sectional area of the capillary tube, disposing the capillary wiper between a test cartridge cover and a sample-receiving chamber in a test cartridge body, obtaining a blood sample using the capillary tube, disposing the capillary tube into and through the capillary wiper whereby the bottom opening of the capillary wiper expands around capillary tube and removes excess blood from an outside surface of the capillary tube as the capillary tube is pushed through the bottom opening thereby reducing over-filling and/or under-filling of the sample into the disposable test cartridge of the point-of-care analyzer, and inserting the disposable test cartridge with sample into the point-of-care analyzer.

In another embodiment of the method of the present invention for reducing erroneous results from a point-of-care analyzer having a disposable test cartridge will now be described. The method includes obtaining a disposable test cartridge designed for the point-of-care analyzer. A finger prick sample is created by lancing a finger of a patient or a urine sample is obtained from the patient depending on the specific test cartridge used, which test cartridges are designed and configured with reagents for specific tests and sample types. For purposes of this explanation, the assumption will be that a blood sample from a finger prick is obtained and the disposable test cartridge specific for this type of sample and associated tests is used. For tests using a urine sample, the method is very similar except that a finger prick is not used. The capillary element is removed from the cartridge cover of the disposable test cartridge. The capillary tube of the capillary element is touched to the drop of blood sample to fill the capillary tube. The capillary element is returned to the disposable test cartridge from which it came. In other words, the capillary element is inserted through the capillary-receiving aperture in the extension portion top surface of the stepped extension portion of the cover extension of the disposable test cartridge and seated in the stepped extension portion. During the insertion and setting process, the capillary tube is inserted through the lower portion aperture located in the apex end of the capillary wiper. Because the cross-sectional area of the lower portion aperture is smaller than the cross-sectional area of the capillary tube, the lower portion aperture acts like a squeegee against the outside surface of the capillary tube and prevents any sample inadvertently disposed on the outside surface of the capillary tube from entering and being deposited into the chamber of test cartridge. The test cartridge is then inserted into the point-of-care analyzer for the automatic testing of the blood sample. Because the capillary wiper removes any sample from the outside surface of the capillary tube, erroneous results are prevented from an "over-filling" of the chamber in the test cartridge with sample. Likewise, since the capillary tube is not wiped by the user, there is no, or very little, chance that any sample within the capillary tube is removed inadvertently, which would lead to erroneous results from an "under-filling" of the chamber in the test cartridge with sample.

DETAILED DESCRIPTION OF THE PRESENT INVENTION

Figure 1:
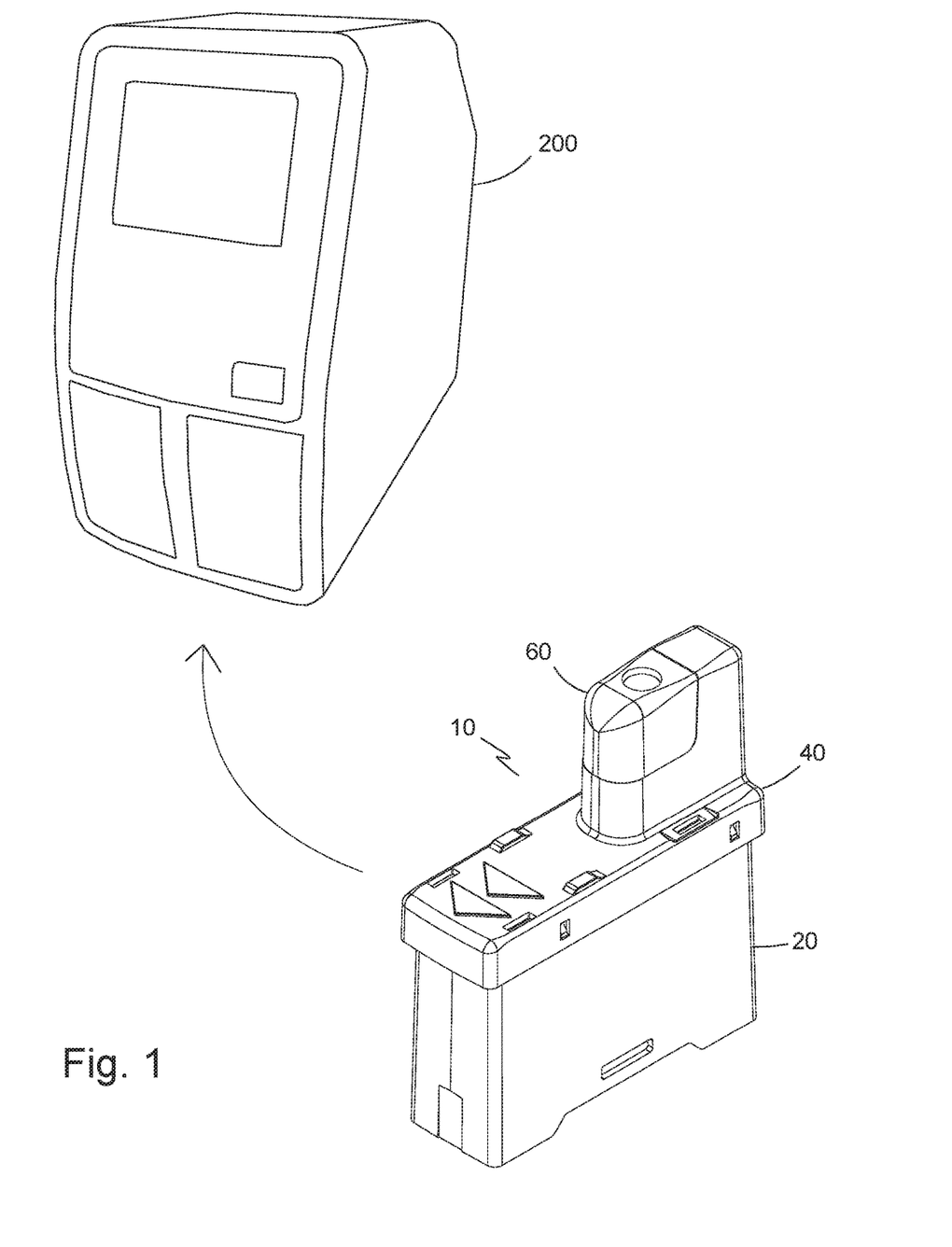
FIG. 1 is a perspective view of one embodiment of the present invention showing a disposable test cartridge for a point-of-care analyzer and a point-of-care analyzer.

The preferred embodiments of the present invention are illustrated in FIGS. 1-19. FIG. 1 shows one embodiment of a disposable test cartridge 10 for use in a point-of-care analyzer 200. Test cartridge 10 includes a cartridge body 20, a cartridge cover 40, a capillary element 60, and a capillary wiper 80 (not shown). Capillary element 60 is removable from the cartridge cover 40.

Figure 2:
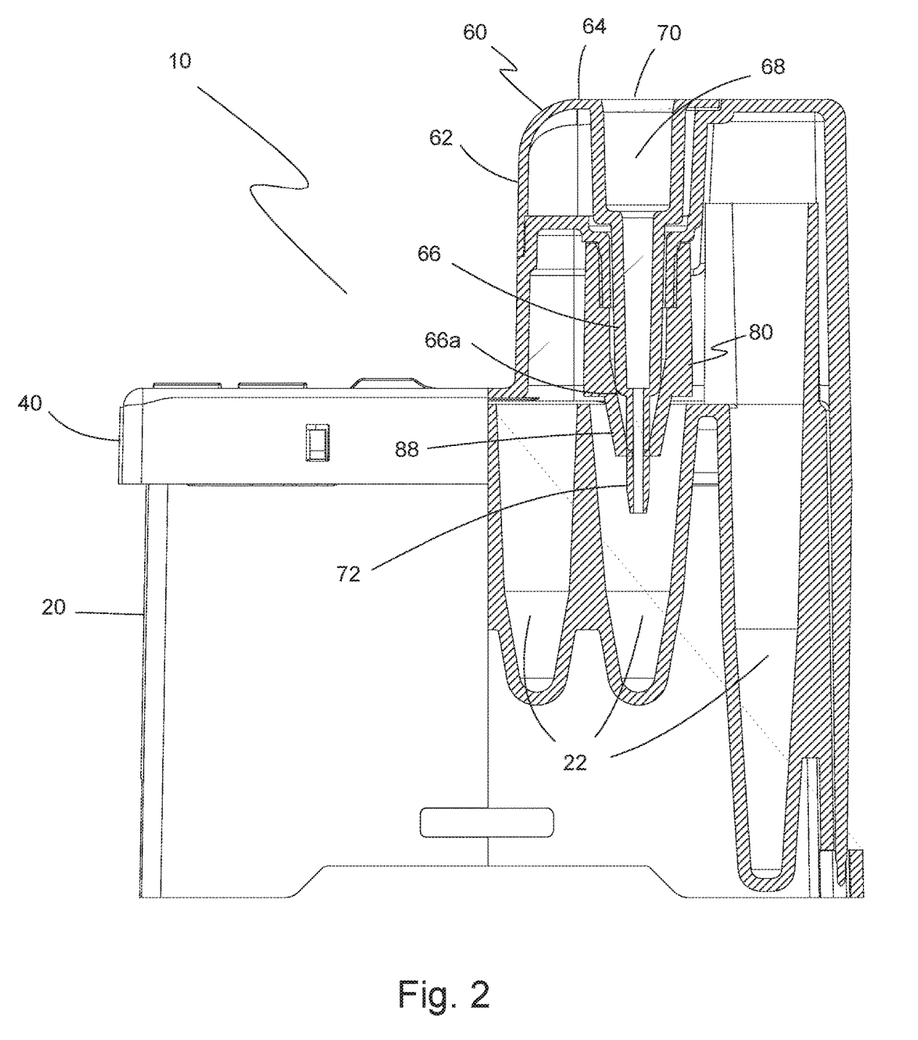
FIG. 2 is an enlarged, partial cross-sectional view of the disposable test cartridge of FIG. 1 showing the capillary wiper.

Turning now to FIG. 2, there is illustrated a partial cross-sectional view of a portion of the disposable test cartridge 10 showing the capillary element 60 and the capillary wiper 80. Capillary element 60 includes a capillary element body 62 having a top body surface 64, a depending capillary element finger 66 defining a capillary element volume 68, a top body opening 70 that communicates with capillary element volume 68, and a capillary tube 72 extending from a finger end 66a. Capillary element volume 68 decreases in cross-sectional area from top body opening 70 to finger end 66a. It is understood that capillary element volume 68 is open and continuous from top body opening 70 and through capillary tube 72. Capillary element volume 68 may have a continuous taper or a stepped taper or a plurality of concentric, reduced diameters. Capillary wiper 80 has an upper portion 82 and a tapered lower portion 88. As can be seen, capillary tube 72 extends through tapered lower portion 88 of capillary wiper 80 and into one of a plurality of chambers 22 within cartridge body 20.

Figures 3, 4:
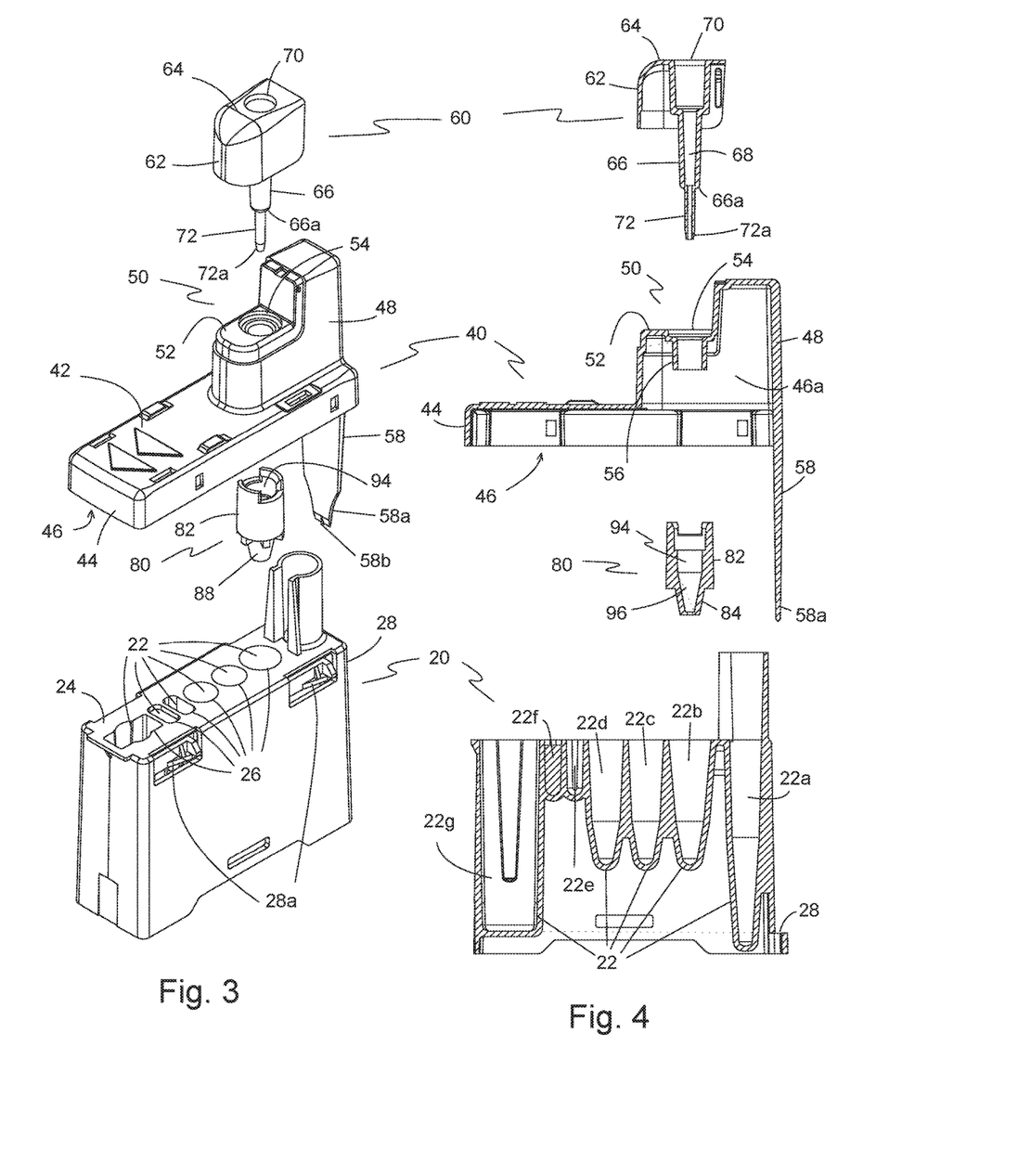
FIG. 3 is an exploded perspective view of the disposable test cartridge of FIG. 1.
FIG. 4 is an exploded side view of the disposable test cartridge of FIG. 1.
Figure 5:
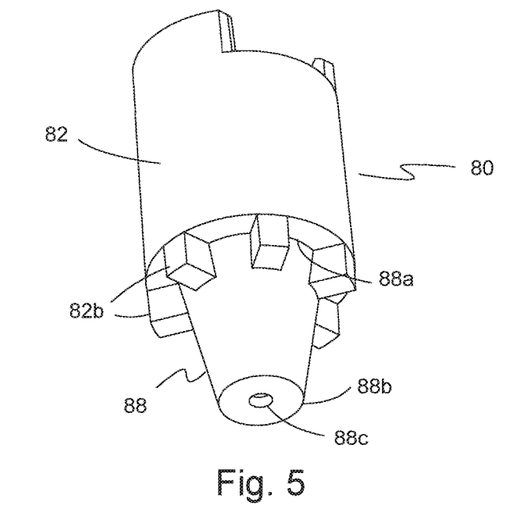
FIG. 5 is an enlarged bottom perspective view of one embodiment of the capillary wiper shown in FIG. 3 showing the tapered lower portion with the lower portion opening.
Figure 6:
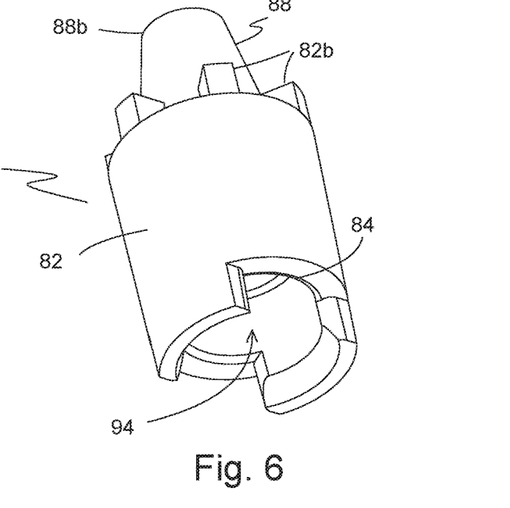
FIG. 6 is an enlarged reverse perspective view of the capillary wiper shown in FIG. 5.
Figure 7:
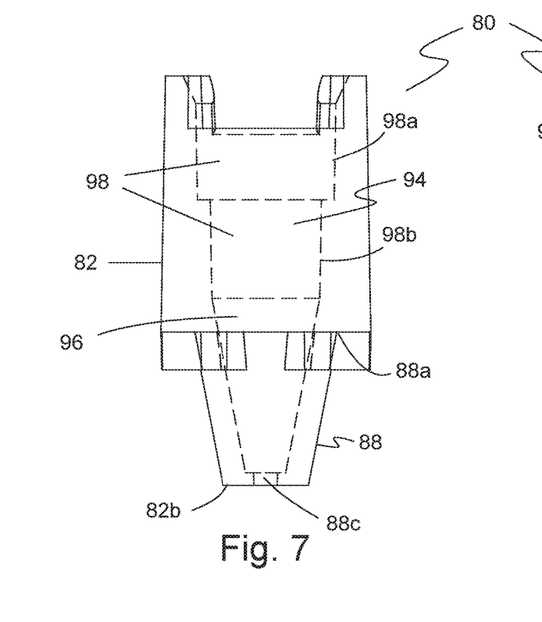
FIG. 7 is an enlarged front plan view of the capillary wiper shown in FIG. 5.
Figure 8:
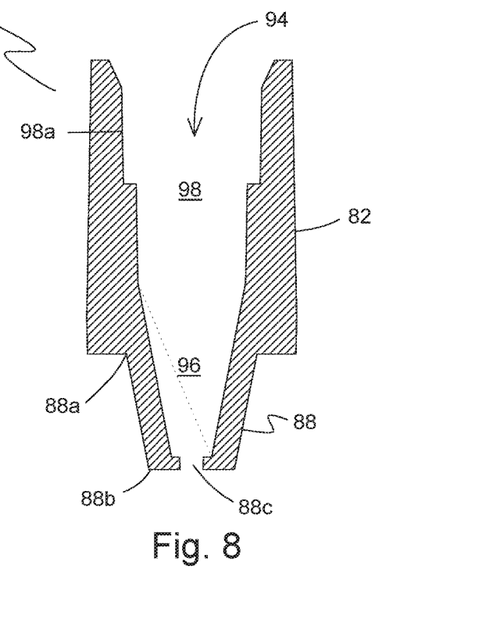
FIG. 8 is an enlarged front cross-sectional view of the capillary wiper shown in FIG. 5.

FIGS. 3 and 4 are exploded views of disposable test cartridge 10 shown in FIG. 1. FIG. 3 is a front perspective view and FIG. 4 is a side cross-sectional view of test cartridge 10. Cartridge body 20 has a plurality of chambers 22 extending below a cartridge body top surface 24, each having an opening 26. Each of the plurality of chambers 22 has a specific purpose such as receiving the test sample, holding a chemical reagent adapted for a specific test, one or more calibration standards, and the like. For example, disposable test cartridge 10 in combination with the point-of-care analyzer may provide test results that include, but are not limited to, HbA1C, eAG, total cholesterol, HDL cholesterol, triglycerides, LDL cholesterol, cholesterol/HDL ratio, non-HDL cholesterol, urine albumin, urine creatinine, and albumin/creatinine ratio. More specifically and referencing FIG. 4, the plurality of chambers 22 of the cartridge body 20 are arranged in the following order. Chamber 22a contains a disposable pipette tip (not shown), chamber 22b is the sample receiving chamber into which capillary tube is inserted and the sample deposited, chamber 22c to 22f contain various reagents for determining a predefined set of test results, and chamber 22g is the mixing and measuring chamber for sample and reagents. Not shown in FIGS. 3 and 4 is a foil seal that covers all of the openings 26 of the plurality of chambers 22 to prevent contamination of the chambers 22 and reagents therein.

Capillary wiper 80 has upper portion 82 and tapered lower portion 88. Upper portion 82 and tapered lower portion 88 are tubular, meaning that capillary wiper 80 defines a capillary wiper volume 94. A lower volume portion 96 is adapted to receive a portion of capillary finger element 66 and capillary tube 72.

Cartridge cover 40 has a cover top surface 42 with a plurality of descending cover sides 44 forming a cover recess 46. Extending upward from cover top surface 42 is cover extension 48 that also forms a recess portion 46a of cover recess 46. Cover extension 48 has a stepped extension portion 50 with an extension portion top surface 52 and a capillary-receiving aperture 54 that communicates with portion 46a of cover recess 46. A cover tube extension 56 extends a predefined distance from capillary-receiving aperture 54 into recess portion 46a. Cover tube extension 56 mates with upper portion 82 of capillary wiper 80. Cover recess 46 receives a top portion 28 of cartridge body 20 and locked in place with releasable tabs 28a. Cartridge cover 40, in this embodiment, also has a back side extension 58 with a back extension end 58a that is received within a cover receiving slot 28 located on cartridge body 20. Back extension end 58a has a small sharp point 58b (more clearly shown in FIG. 3) that is used by the point-of-care analyzer to pierce the foil covered openings 26 of the plurality of chambers 22 during use of the disposable test cartridge 10. The pipette tip (not shown) is used by the analyzer to dilute the sample and select a predefined quantity of the diluted sample for mixing with the test reagents and subsequent measurement in chamber 22g. It is understood that the analyzer removes cartridge cover 40 and uses the back extension end 58a to pierce the foil seal once the capillary tube 72 and sample are inserted into and assembled with cartridge cover 40 and then the disposable test cartridge 10 is inserted into the analyzer 200.

As previously discussed, capillary element 60 has element body 62, top body surface 64, depending capillary element finger 66 defining a capillary element volume 68, top body opening 70 that communicates with capillary element volume 68, and a capillary tube 72 extending from a finger end 66a. Capillary tube 72 has a tube distal end 72a that may optionally be tapered.

Turning now to FIGS. 5-8, there is illustrated various enlarged views of capillary wiper 80. Capillary wiper 80 has two major portions, the upper portion 82 and a tapered lower portion 88. Tapered lower portion 88 has a base end 88a and an apex end 88b where apex end 88b has lower portion aperture 88c. At the junction between upper portion 82 and tapered lower portion 88, there are a plurality of optional upper portion protrusions 82b that extend in the same direction as tapered lower portion 88. Upper portion protrusions 82 are spaced from each other in a radial array that provides a limited amount of compressibility. Upper portion protrusions 82 tend to stabilize cartridge wiper 80 when assembled between cartridge cover 40 and cartridge body 20.

Capillary wiper volume 94 has lower volume portion 96 and an upper volume portion 98 in communication with lower volume portion 96. Lower volume portion 96 is optionally tapered from its junction with upper volume portion 98 to lower portion aperture 88c. One advantage of having a tapered lower volume portion 96 is it provides a centering guide for capillary tube 72. It is contemplated that an untapered cylindrical volume having a cross-sectional diameter greater than capillary tube 72 may also be used. In the embodiment illustrated, upper volume portion 98 is divided into two different cross-sectional areas, 98a and 98b, but could also have only one or more that two different cross-sectional areas depending on the structural configuration of cartridge cover 40. In the embodiment illustrated, upper volume portion 98a has a larger cross-sectional diameter than upper volume portion 98b to better fit over cover tube extension 56 and provides a snug fit so that cover tube extension 56 retains capillary wiper 80 when cartridge cover 40 is removed during processing of the sample in disposable test cartridge 10 by point-of-care analyzer 200.

Figure 9:
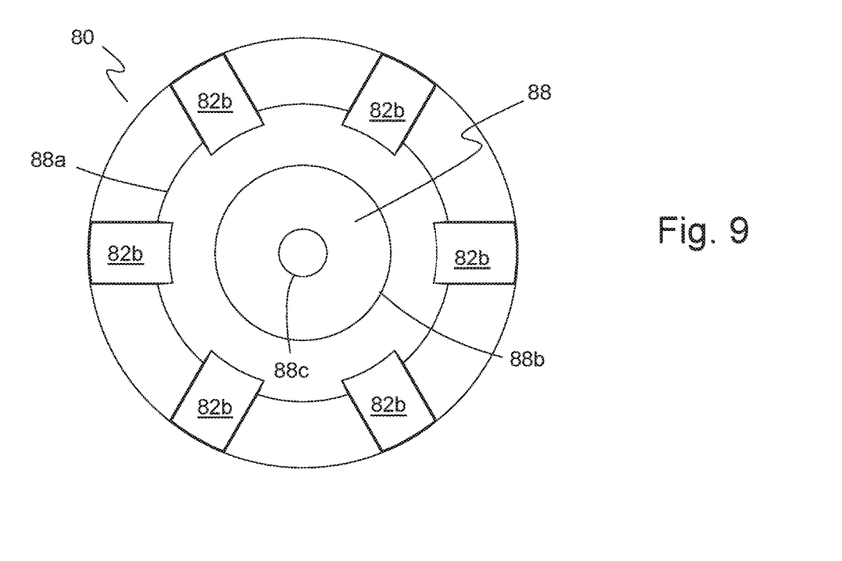
FIG. 9 is an enlarged bottom view of the capillary wiper shown in FIG. 5.
Figure 10:
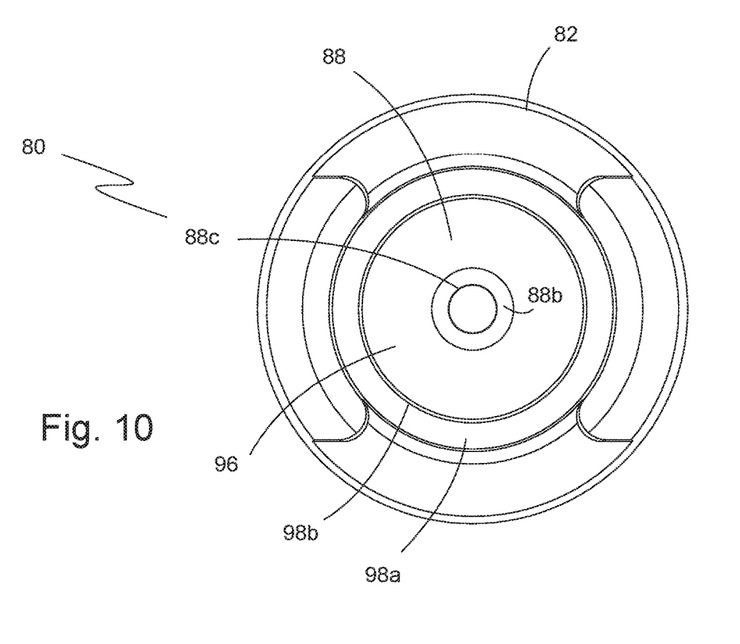
FIG. 10 is an enlarged top view of the capillary wiper shown in FIG. 5.

FIG. 9 illustrates a distal end view of capillary wiper 80. In this view, the radial positioning of optional upper portion protrusions 82b is clearly shown. Apex end 88b includes lower portion aperture 88c and tapered lower portion 88. FIG. 10 illustrates a proximal end view of capillary wiper 80. In this view, the concentric nature of capillary wiper volume 94 is shown. At the furthest point, there is shown lower portion aperture 88c and apex end 88b. Tapered lower portion 88 in this embodiment defines lower volume portion 96 as having a tapered shape which extends from upper volume portion 98 to apex end 88b. In this embodiment, upper volume portion 98 is divided into upper volume portion 98a and upper volume portion 98b.

Figure 11:
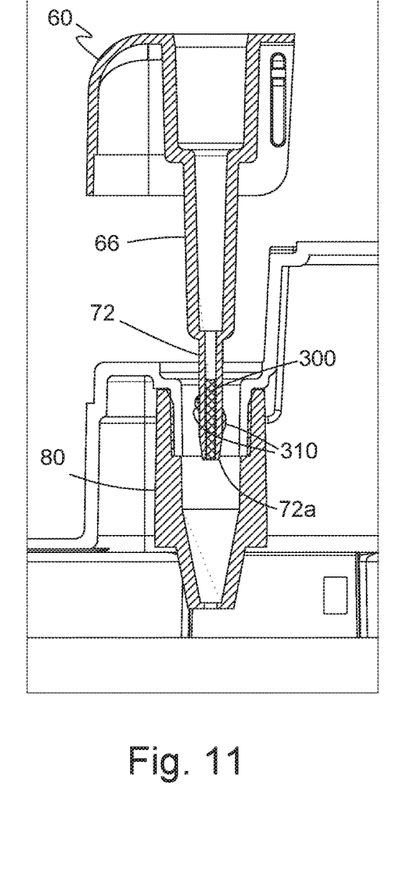
FIG. 11 is an enlarged cross-sectional view of the capillary element containing a sample and being inserted into the cartridge cover and capillary wiper.
Figure 12:
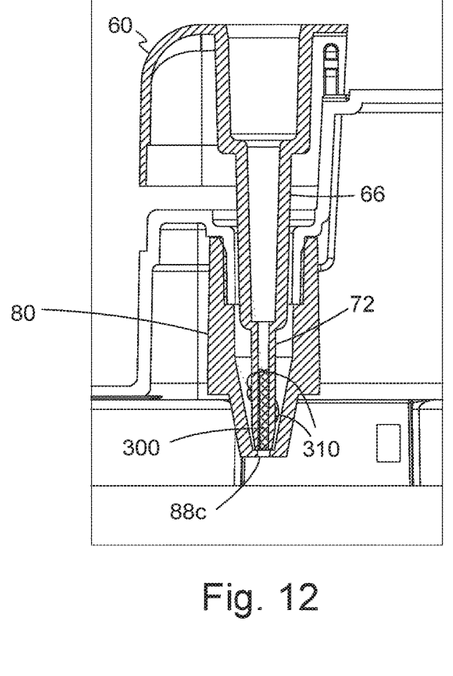
FIG. 12 is an enlarged cross-sectional view of the capillary element containing a sample and being inserted into the cartridge cover and capillary wiper showing the capillary tip about to push through the capillary wiper.
Figure 13:
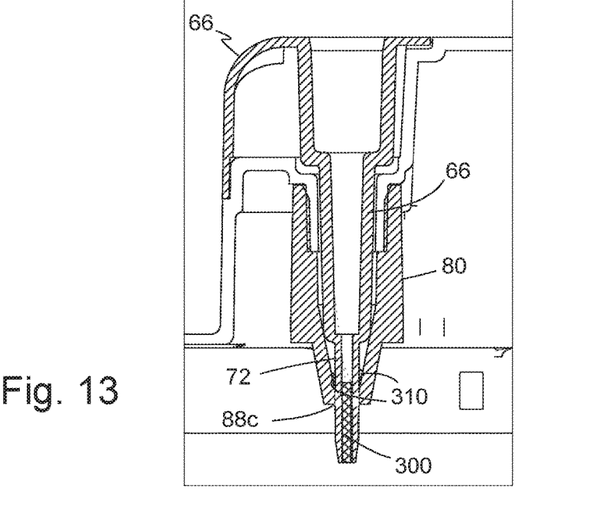
FIG. 13 is an enlarged cross-sectional view of the capillary element containing a sample and being inserted into the cartridge cover and capillary wiper showing the capillary tube extending through the capillary wiper.

Turning now to FIGS. 11-13, there is illustrated capillary tube 72 containing a sample 300 to be tested where the sample for testing is inside capillary tube 72 and sample 310 on the outside surface of capillary tube 72. It is this sample 310 on the outside surface of capillary tube 72 that potentially leads to erroneous test results. Typically, a trained technologist would carefully wipe the outside of capillary tube 72 to remove the sample 310 on the outside surface of capillary tube 72, being careful not to touch tube distal end 72a. If the sample 310 on the outside surface is not removed, the transfer of the sample 300 and 310 into the dilution chamber 22b would cause the sample to have a higher ratio of sample to diluent thus causing the test results to have higher values than they should have. If the distal end 72a is accidentally touched while wiping the outside surface of capillary tube 72, an amount of sample within capillary tube 72 may be withdrawn leaving a smaller amount of sample available for dilution. This causes the sample to have lower values than they should have. Because point-of-care analyzer is designed to provide accurate measurements based on a specific predefined sample size, any over-filling of sample in the dilution chamber 22b caused by sample remaining on the outside surface of capillary tube 72 or any under-filling of sample in dilution chamber 22b caused by the inadvertent removal of a small amount of sample from the capillary tube 72 leads to erroneous results. This is even more of a problem for point-of-care analyzers since these types of analyzers are for use in a doctor's office, which do not employ highly trained technologists, who are used typically in central labs where hundreds of tests are run daily. These highly trained technologists have the techniques that ensure consistent results. The typical person in a doctor's office that would obtain the blood and/or urine sample for measurement by the point-of-care analyzer have other duties such as nurses, physician assistants, medical assistants, and the like that are not highly trained as lab technologists. The consequence is a higher number of inaccurate and erroneous results that could lead to improper diagnose and treatment of patients.

Sample Data Showing Erroneous Results

The use of capillary wiper 80 provides a marked improvement in results obtained from a point-of-care analyzer when operated by persons other than a trained instrument technologist. Two sets of test data were obtained using a point-of-care analyzer (Allegro by Nova Biomedical Corporation). The first set involved the use of a disposable test cartridge without the integral capillary wiper 80 and the second set involved the use of a test cartridge with the integral capillary wiper 80. To simulate the effect of using a person that is not a trained instrument technologist, some of the capillary tubes 72 were intentionally over dosed with sample so that some sample was left on the outside surface of the capillary tube. This simulates the improper wiping and/or lack of wiping the outside surface of the capillary tube after obtaining a sample for testing. The tests consisted of ten (10) whole blood samples run with the integral capillary wiper 80 and ten (10) whole blood samples run without the integral capillary wiper. Measurements were made for total cholesterol (TC), triglycerides (TG), and high-density lipo-proteins (HDL). Standard deviation (STDEV), average value (AVG) and percent coefficient of variation (%CV) were determined for all sample points, for overdosed capillary tubes and for properly dosed capillary tubes for each set of test measurements.

Table 1 below contains the test data for the samples run using a disposable test cartridge with no capillary wiper. The letters "OD" under method represents a test sample with a capillary tube having sample on its outside surface (i.e. overdosed).

TABLE 1

| Sample | TC mg/dL | TG mg/dL | HDL mg/dL | Method |
|---|---|---|---|---|
| 1 | 257 | 81 | 77 | OD |
| 2 | 177 | 75 | 51 | |
| 3 | 225 | 80 | 67 | OD |
| 4 | 182 | 56 | 51 | |
| 5 | 184 | 62 | 51 | OD |
| 6 | 179 | 61 | 45 | |
| 7 | 226 | 69 | 63 | OD |
| 8 | 174 | 59 | 48 | |
| 9 | 205 | 61 | 52 | OD |
| 10 | 167 | 59 | 42 | |

Table 2 is discloses the standard deviation, average values and percent coefficient of variation for the values in Table 1.

TABLE 2

| All Points | | | |
|---|---|---|---|
| STDEV | 29.5 | 9.3 | 10.9 |
| AVG | 197.6 | 66.3 | 54.7 |
| % CV | 14.9% | 14.0% | 19.9% |
| Overdosed Capillaries | | | |
| STDEV | 27.2 | 9.6 | 10.9 |
| AVG | 219.4 | 70.6 | 62.0 |
| % CV | 12.4% | 13.5% | 17.5% |
| Properly dosed Capillaries | | | |
| STDEV | 5.7 | 7.5 | 3.9 |
| AVG | 175.8 | 62.0 | 47.4 |
| % CV | 3.3% | 12.1% | 8.3% |

Figure 14:
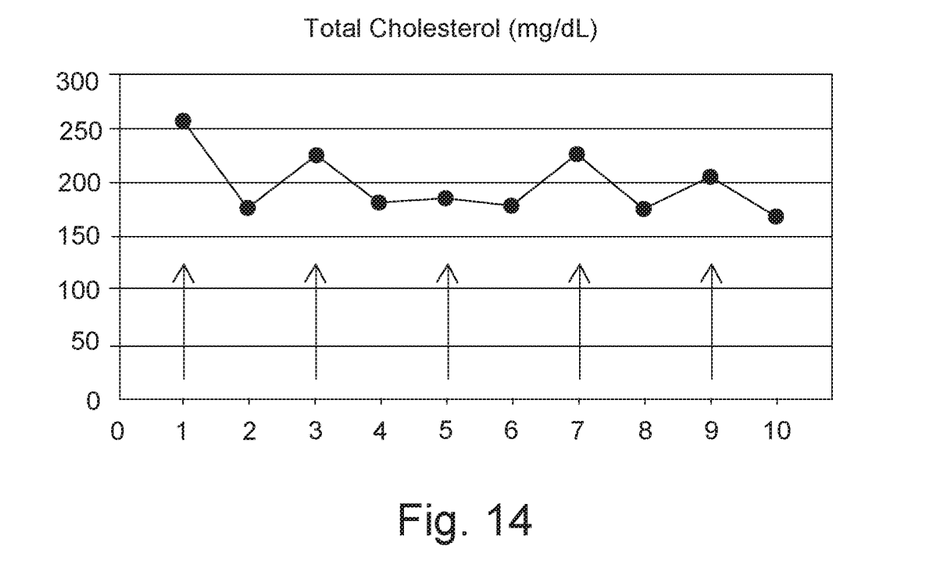
FIG. 14 is a graphic representation of the data in Table 1 showing the results for total cholesterol where a capillary wiper was not included in the disposable test cartridge.
Figure 15:
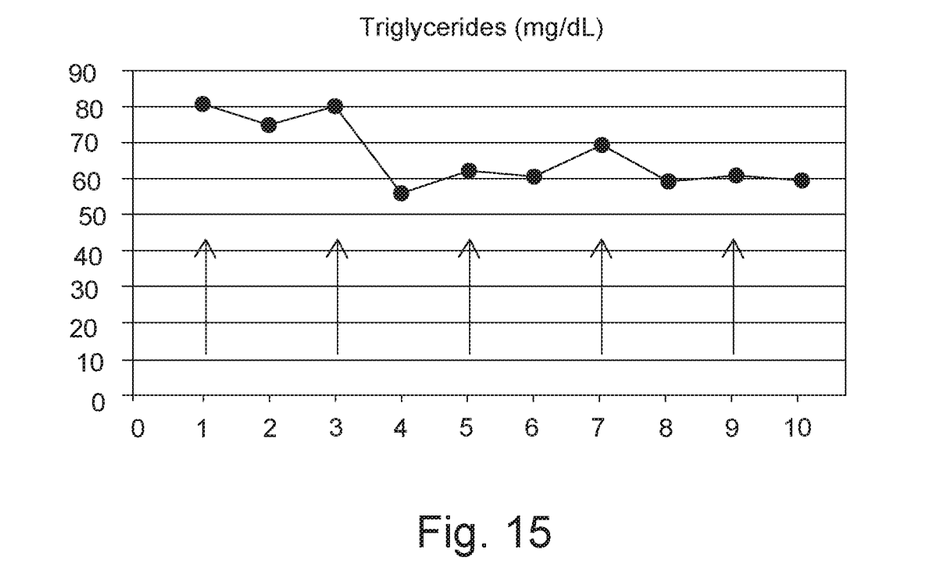
FIG. 15 is a graphic representation of the data in Table 1 showing the results for triglycerides where a capillary wiper was not included in the disposable test cartridge.
Figure 16:
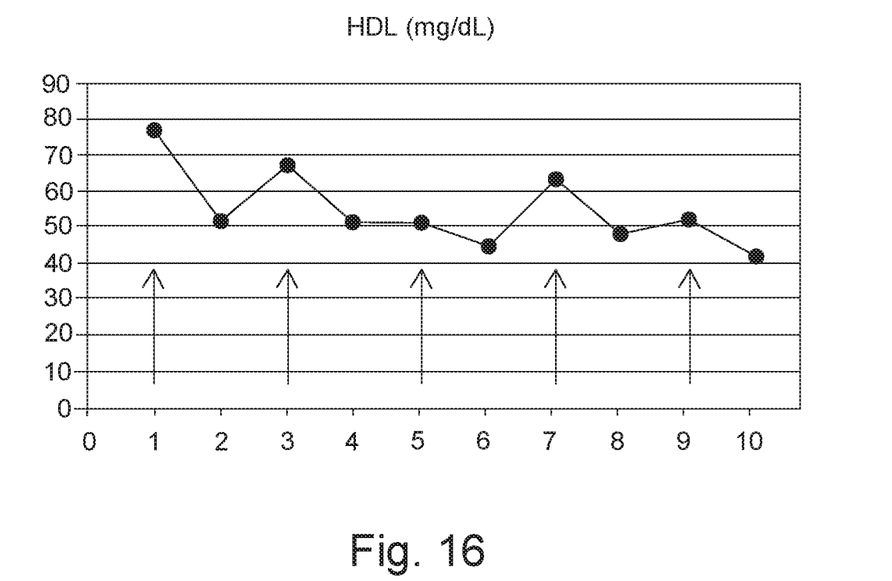
FIG. 16 is a graphic representation of the data in Table 1 showing the results for high-density lipoproteins where a capillary wiper was not included in the disposable test cartridge.

FIGS. 14-16 are schematic representations of the test data for each category (i.e. TC, TG and HDL) disclosed in Table 1. Indicators were added to the drawings to bring attention to those values for the capillary tubes that had sample on the outside surface. As can be seen from the test data, each of the 'overdosed' capillaries (indicated by arrows in the FIGS. 14-19) reported higher values for total cholesterol, triglycerides and high-density lipo-proteins. Even the values for all tests (both standard dose and over-dosed samples) taken together reported higher values for total cholesterol, triglycerides and high-density lipo-proteins than for the properly-dosed capillaries only. The standard deviations, the average values and the percent coefficient of variation had significantly higher values for the capillary tubes with sample on the outside surface (i.e. overdosed capillaries) than the values for the capillary tubes that were properly dosed.

Table 3 below contains the test data for the samples run using a disposable test cartridge with a capillary wiper.

TABLE 3

| Sample | TC mg/dL | TG mg/dL | HDL mg/dL | Method |
|---|---|---|---|---|
| 1 | 169 | 69 | 40 | OD |
| 2 | 173 | 63 | 41 | |
| 3 | 177 | 62 | 51 | OD |
| 4 | 176 | 63 | 46 | |
| 5 | 174 | 69 | 44 | OD |
| 6 | 180 | 62 | 50 | |

TABLE 3-continued

| Sample | TC mg/dL | TG mg/dL | HDL mg/dL | Method |
|---|---|---|---|---|
| 7 | 173 | 62 | 51 | OD |
| 8 | 177 | 61 | 49 | |
| 9 | 174 | 64 | 41 | OD |
| 10 | 174 | 71 | 42 | |

Table 4 discloses the standard deviation, average values and percent coefficient of variation for the values in Table 3.

TABLE 4

| All Points | | | |
|---|---|---|---|
| STDEV | 3.0 | 3.6 | 4.5 |
| AVG | 174.7 | 64.6 | 45.5 |
| % CV | 1.7% | 5.6% | 9.8% |
| Overdosed Capillaries | | | |
| STDEV | 2.9 | 3.6 | 5.3 |
| AVG | 173.4 | 65.2 | 45.4 |
| % CV | 1.7% | 5.5% | 11.7% |
| Properly dosed Capillaries | | | |
| STDEV | 2.7 | 4.0 | 4.0 |
| AVG | 176.0 | 64.0 | 45.6 |
| % CV | 1.6% | 6.3% | 8.9% |

Figure 17:
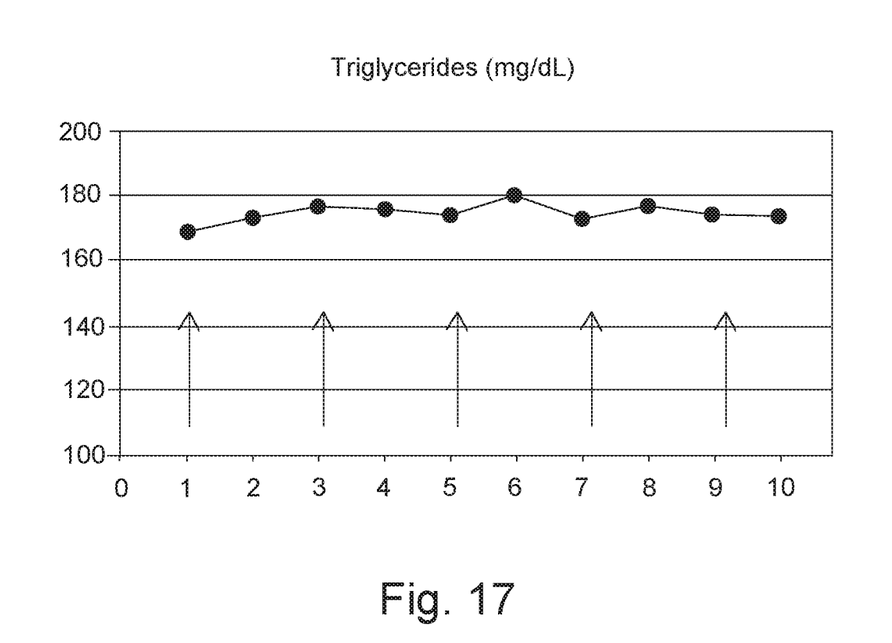
FIG. 17 is a graphic representation of the data in Table 3 showing the results for total cholesterol where a capillary wiper was included in the disposable test cartridge.
Figure 18:
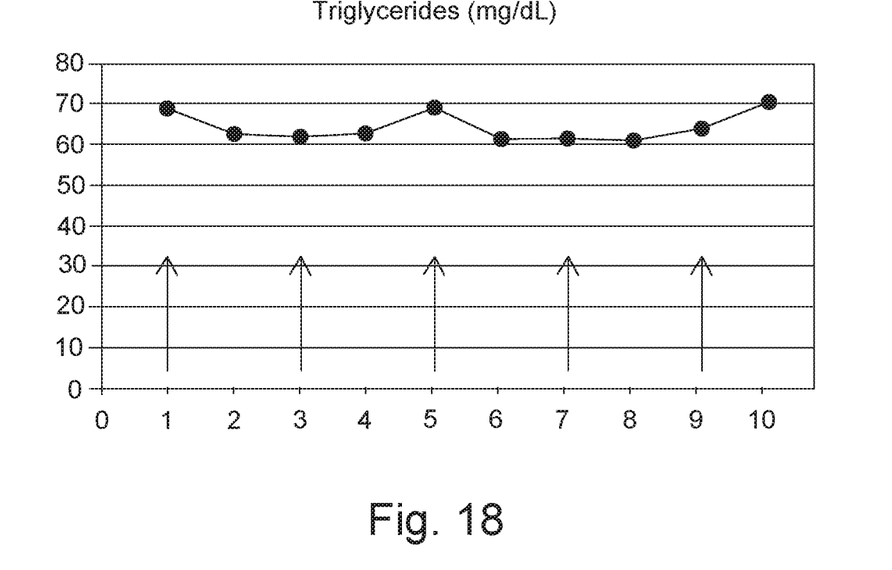
FIG. 18 is a graphic representation of the data in Table 3 showing the results for triglycerides where a capillary wiper was included in the disposable test cartridge.
Figure 19:
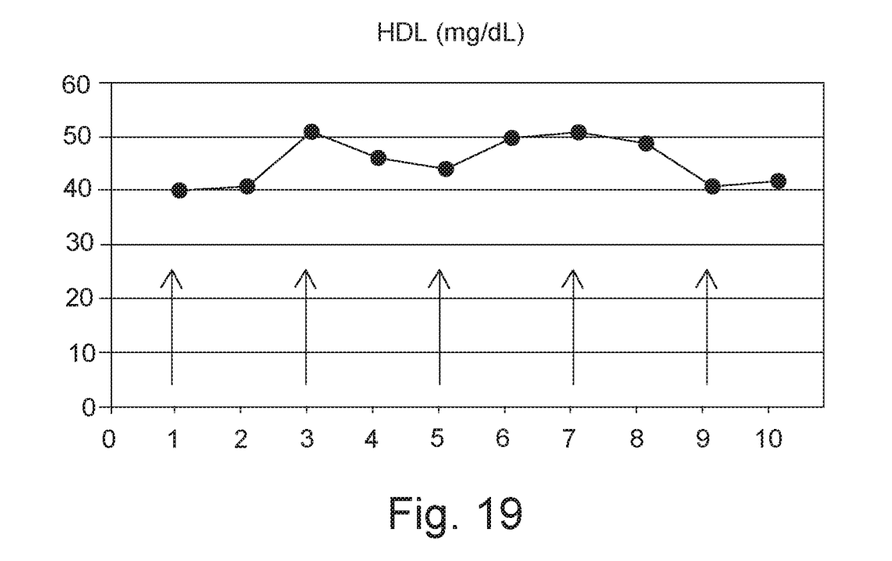
FIG. 19 is a graphic representation of the data in Table 3 showing the results for high-density lipoproteins where a capillary wiper was included in the disposable test cartridge.

FIGS. 17-19 are schematic representations of the test data for each category (i.e. TC, TG and HDL) disclosed in Table 3. Indicators were added to the drawings to bring attention to those values for the capillary tubes that had sample on the outside surface. As can be seen from the test data, each of the 'overdosed' capillaries reported very similar values for total cholesterol, triglycerides and high-density lipo-proteins. Even the values for all tests (both standard dose and over-dosed samples) taken together reported similar values for total cholesterol, triglycerides and high-density lipo-proteins to those for the properly-dosed capillaries only. The standard deviations, the average values and the percent coefficient of variation had significantly similar values for the capillary tubes with sample on the outside surface (i.e. overdosed capillaries) to the values for the capillary tubes that were properly dosed.

The conclusion from this test data is that the use of a disposable test cartridge containing a capillary wiper provides consistently better and fewer erroneous results. Accordingly, even when a person that is not trained as an instrument technologist performs the acquisition and testing of a sample using a capillary tube for a point-of-care analyzer, the lack of wiping any excess sample from the capillary tube before inserting the capillary tube with sample into the disposable test cartridge still provides relatively accurate results as seen from the standard deviation, average value and percent coefficient of variation between the over-dosed and properly dosed capillary tubes. Furthermore, not wiping the outside surface of capillary tube 72 prevents the inadvertent and accidental removal of sample from inside capillary tube 72.

A method of reducing erroneous results from a point-of-care analyzer 200 having a disposable test cartridge 10 for receiving a test sample will now be discussed. The method includes providing a tubular, capillary wiper 80 having a pipette-shaped longitudinal cross-section with a tapered, elastomeric bottom portion 88 and a top opening 84 having a cross-sectional area greater than the cross-sectional area of a capillary tube 72 used with the disposable test cartridge 10 and a bottom opening 88c having a cross-sectional area smaller than the cross-sectional area of the capillary tube 72. The method also includes disposing the capillary tube 72 into and through the capillary wiper 80 whereby the bottom opening 88c of the capillary wiper 80 expands around capillary tube 72 and removes excess sample from an outside surface of the capillary tube 72 as the capillary tube 72 is pushed through the bottom opening 88c and prevents the excess sample from being added to or with the sample within the capillary tube 72.

For the illustrated disposable test cartridge 10, the method will now be discussed. A disposable test cartridge 10 designed for the point-of-care analyzer 200 is obtained. A finger prick sample is created by lancing a finger of a patient or a urine sample is obtained from the patient depending on the specific test cartridge 10 used, which are designed and configured with reagents for specific tests and sample types. For purposes of this explanation, the assumption will be that a blood sample from a finger prick is obtained and the disposable test cartridge 10 specific for this type of sample and associated tests is used. For tests using a urine sample, the method is very similar except that a finger prick is not used. The capillary element 60 is removed from cartridge cover 40 of disposable test cartridge 10. Capillary tube 72 of capillary element 60 is touched to the drop of blood sample to fill capillary tube 72. Capillary element 60 is returned to disposable test cartridge from which it came. In other words, capillary element 60 is inserted through capillary-receiving aperture 54 in extension portion top surface 52 of stepped extension portion 50 of cover extension 48 of disposable test cartridge 10 and seated in stepped extension portion 50. During the insertion and setting process, capillary tube 72 is inserted through lower portion aperture 88c located in apex end 88b of capillary wiper 80. Because the cross-sectional area of lower portion aperture 88c is smaller than the cross-sectional area of capillary tube 72, lower portion aperture 88c acts like a squeegee against the outside surface of capillary tube 72 and prevents any sample inadvertently disposed on the outside surface of capillary tube 72 from entering and being deposited into chamber 22b of test cartridge 10. Cartridge 10 is then inserted into point-of-care analyzer 200 for the automatic testing of the sample. Because capillary wiper 80 removes any sample from the outside surface of capillary tube 72, erroneous results are prevented from an "over-filling" of chamber 22b with sample. Likewise, since capillary tube 72 is not wiped by the user, there is no, or very little, chance that any sample within capillary tube 72 is removed inadvertently, which would lead to erroneous results from an "under-filling" of chamber 22b with sample.

Thus, the present invention provides a point-of-care analyzer with disposable test cartridge(s) that can be used by persons other than a highly trained instrument technologist and still obtain accurate results in a timely manner in a doctor office setting similar to the results obtained from tests performed by highly trained instrument technologists in central testing laboratories.

Although the preferred embodiments of the present invention have been described herein, the above description is merely illustrative. Further modification of the invention herein disclosed will occur to those skilled in the respective arts and all such modifications are deemed to be within the scope of the invention as defined by the appended claims.

What is claimed is:

1. A disposable test cartridge for a point-of-care analyzer, the test cartridge comprising:

a cartridge body having a plurality of chambers wherein each of the plurality of chambers has an opening at a top of the cartridge body;

a cartridge cover connected to the cartridge body, the cartridge cover having a capillary-receiving aperture and a cover tube extension extending from the capillary-receiving aperture a predefined distance towards but spaced from the cartridge body;

an elastomeric tubular capillary wiper defines an internal through space and is aligned with the capillary-receiving aperture wherein the tubular capillary wiper and the capillary-receiving aperture are aligned with one of the plurality of chambers of the cartridge body, the tubular capillary wiper having a tubular upper portion with an upper portion opening and a tapered lower portion with a lower portion opening; and a capillary element removably insertable into the cartridge cover, the capillary element having a capillary tube that extends into the capillary-receiving aperture and through the tubular capillary wiper wherein a tip portion of the capillary tube extends through the lower portion opening and into the one of the plurality of chambers of the cartridge body, wherein the lower portion opening has a diameter smaller than an outside diameter of the capillary tube and expands around the capillary tube.

2. The disposable test cartridge of claim 1, wherein the internal through space within the tapered lower portion is tapered.

3. The disposable test cartridge of claim 1, wherein the capillary element has a capillary element body with a top body opening in fluid communication with the capillary tube.

4. The disposable test cartridge of claim 1, wherein the tubular upper portion of the capillary wiper has a cylindrical recess with a diameter smaller than a diameter of the cover tube extension of the cartridge cover.

5. The disposable test cartridge of claim 1, wherein the tubular upper portion has a lower tubular end that transitions to the tapered lower portion, the lower tubular end having a ledge portion that contacts the top of the cartridge body while the tapered lower portion extends into the one of the plurality of chambers of the cartridge body.

6. The disposable test cartridge of claim 1, wherein the capillary wiper has a pipette shape with a circular cross-section.

7. A method to reduce erroneous results from a point-of-care blood analyzer caused by over-filling and under-filling of a sample disposed in the disposable test cartridge of claim 1, the method comprising:

providing the disposable test cartridge of claim 1;

obtaining a blood sample using the capillary tube used with the disposable test cartridge;

disposing the capillary tube into and through the capillary wiper whereby the lower portion opening of the capillary wiper expands around capillary tube and removes excess blood from an outside surface of the capillary tube as the capillary tube is pushed through the lower portion opening thereby reducing over-filling and/or under-filling of the sample into the disposable test cartridge; and inserting the disposable test cartridge with sample into the point-of-care analyzer.

8. The method of claim 7, wherein the step of obtaining the blood sample includes removing the capillary element containing the capillary tube from the cartridge cover before obtaining the blood sample.

9. The method of claim 7, wherein the step of obtaining the blood sample includes performing a finger stick to produce a small blood sample and touching the capillary tube to the blood sample to transfer a predefined quantity of blood from the blood sample into the capillary tube.

\* \* \* \* \*